United States Patent
Churchill et al.

(10) Patent No.: US 10,117,710 B2
(45) Date of Patent: Nov. 6, 2018

(54) ENDOMETRIAL LINING TISSUE TREATMENT DEVICE

(71) Applicant: HOLOGIC, INC., Marlborough, MA (US)

(72) Inventors: William Lucas Churchill, Bolton, MA (US); Catherine Withers, Marlborough, MA (US); Matthew LaPlaca, Cumberland, RI (US); Victor M. Solano Umaña, Alajuela (CR)

(73) Assignee: Hologic, Inc., Marlborough, MA (US)

( * ) Notice: Subject to any disclaimer, the term of this patent is extended or adjusted under 35 U.S.C. 154(b) by 465 days.

(21) Appl. No.: 14/876,515

(22) Filed: Oct. 6, 2015

(65) Prior Publication Data

US 2016/0095648 A1 Apr. 7, 2016

Related U.S. Application Data

(60) Provisional application No. 62/061,081, filed on Oct. 7, 2014.

(51) Int. Cl.
*A61B 18/14* (2006.01)
*A61M 25/10* (2013.01)
(Continued)

(52) U.S. Cl.
CPC ..... *A61B 18/1485* (2013.01); *A61M 25/1002* (2013.01); *A61B 2017/4225* (2013.01);
(Continued)

(58) Field of Classification Search
CPC ........ A61B 18/1485; A61B 2017/4225; A61B 2218/007; A61B 2018/00214;
(Continued)

(56) References Cited

U.S. PATENT DOCUMENTS 4,160,446 A 7/1979 Barrington
6,245,067 B1 6/2001 Tu et al.
(Continued)

OTHER PUBLICATIONS

Communication under Rule 71(3) for European Patent Application No. 15781558.0, dated Nov. 2, 2017, Applicant Hologic, Inc. 7 pages.

(Continued)

*Primary Examiner* — Thomas Giuliani
(74) *Attorney, Agent, or Firm* — Vista IP Law Group, LLP

(57) ABSTRACT

An endometrial tissue treatment device includes an elongate positioning member and an energy applicator coupled to a distal end of the positioning member, the energy applicator including a tissue contacting member and an expandable-collapsible support structure underlying the tissue contacting member, the expandable-collapsible support structure comprising a substantially non-compliant elongate balloon disposed within the tissue contacting member that, when inflated, has a length oriented substantially transverse to the positioning member, including a first closed end that positions a corresponding first corner portion of the tissue contacting member in a first cornu of a uterine cavity, and a second closed end that positions a corresponding second corner portion of the tissue contacting member in a second cornu of a uterine cavity, with a lengthwise portion of the balloon positioning a distal facing portion of the tissue contacting member for contacting a fundal wall of a uterus.

14 Claims, 12 Drawing Sheets

(51) Int. Cl.
*A61B 18/00* (2006.01)
*A61B 17/42* (2006.01)

(52) U.S. Cl.
CPC .......... *A61B 2018/0022* (2013.01); *A61B 2018/00559* (2013.01); *A61B 2018/1475* (2013.01); *A61B 2218/007* (2013.01)

(58) Field of Classification Search
CPC .. A61B 2018/0022; A61B 2018/00232; A61B 2018/00238; A61B 2018/00255; A61B 2018/00559; A61B 2018/1475; A61B 2018/00196; A61B 2018/00285; A61M 25/1002
USPC .......................... 606/41; 607/113, 116, 138
See application file for complete search history.

(56) References Cited

U.S. PATENT DOCUMENTS

| | | |
|---|---|---|
| 6,508,815 B1 | 1/2003 | Strul et al. |
| 6,813,520 B2 | 11/2004 | Truckai et al. |
| 2005/0085880 A1* | 4/2005 | Truckai .............. A61B 18/1485 607/101 |
| 2005/0177147 A1* | 8/2005 | Vancelette ............. A61B 18/02 606/21 |
| 2007/0088344 A1 | 4/2007 | Schechter et al. |
| 2008/0249534 A1* | 10/2008 | Gruber .................. A61B 1/303 606/119 |
| 2009/0125010 A1* | 5/2009 | Sharkey ................ A61B 18/04 606/27 |
| 2009/0299327 A1* | 12/2009 | Tilson ................ A61B 17/8816 604/500 |
| 2010/0228239 A1* | 9/2010 | Freed ................. A61B 18/1485 606/27 |
| 2011/0118718 A1 | 5/2011 | Toth et al. |
| 2011/0301584 A1 | 12/2011 | Beck et al. |
| 2012/0265197 A1 | 10/2012 | Truckai et al. |
| 2013/0158536 A1* | 6/2013 | Bloom .............. A61B 18/1492 606/33 |

OTHER PUBLICATIONS

PCT International Search Report and Written Opinion for International Publication No. PCT/US2015/054284, Applicant Hologic, Inc., Forms PCT/ISA/210, 220, and 237, dated Jan. 13, 2016 (12 pages).

Amendment and Response to Non-Final Rejection dated Jul. 7, 2014, for U.S. Appl. No. 13/267,258, filed Oct. 6, 2011, response submitted Dec. 15, 2014. (6 pages).

* cited by examiner

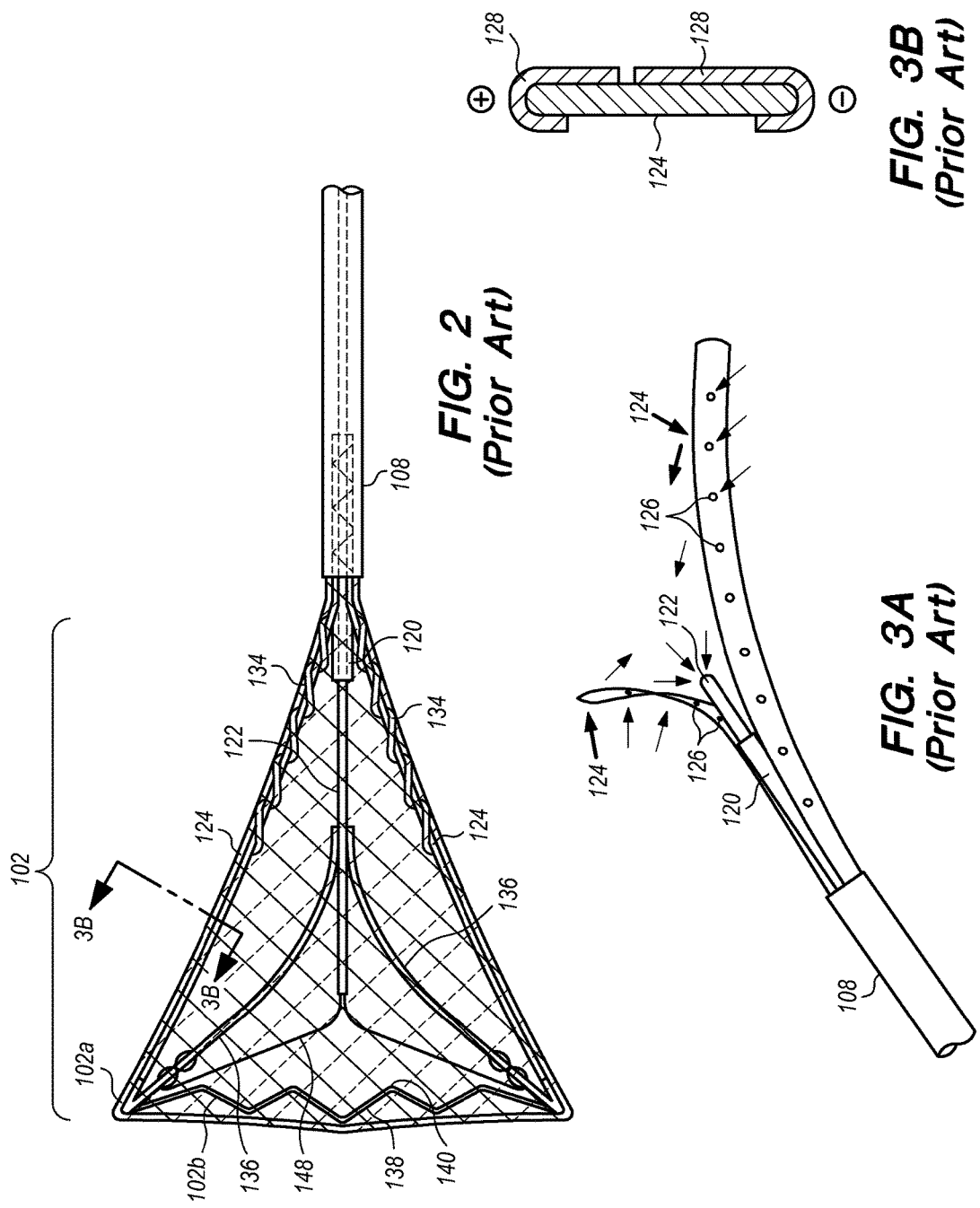

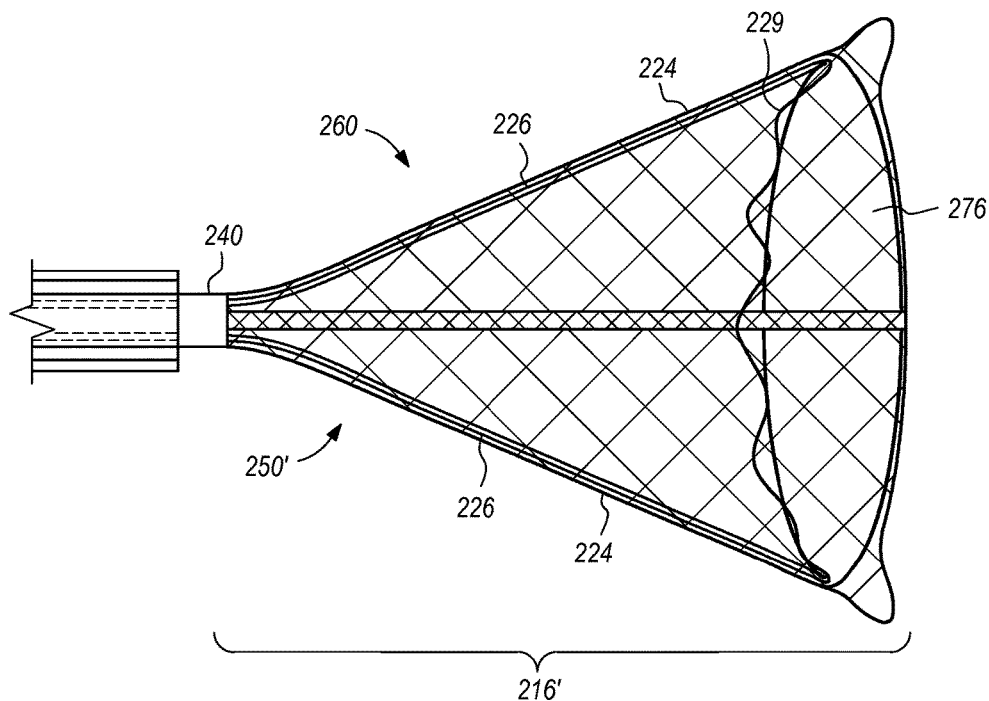
FIG. 10
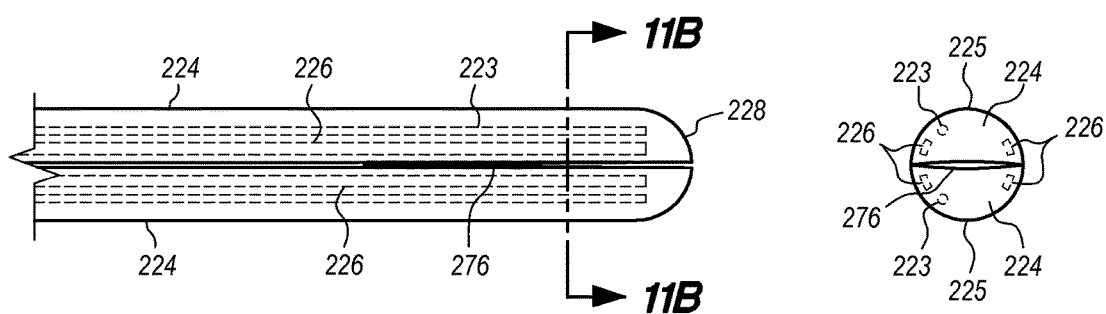
FIG. 11A  FIG. 11B

ENDOMETRIAL LINING TISSUE TREATMENT DEVICE

RELATED APPLICATION DATA

The present application claims the benefit under 35 U.S.C. § 119 to U.S. provisional patent application Ser. No. 62/061,081, filed Oct. 7, 2014. The foregoing application is hereby incorporated by reference into the present application in its entirety.

FIELD OF INVENTION

The disclosed inventions pertain generally to systems and methods for treating the interior surfaces of body organs, such as the endometrial lining tissue of the uterus.

BACKGROUND

Thermal ablation of the interior lining of a body organ is a procedure which involves heating the organ lining to a temperature that destroys the cells of the lining tissue. Such a procedure may be performed as a treatment to one of many conditions, such as menorrhagia, which is characterized by chronic bleeding of the endometrial tissue layer of the uterus. Existing methods for effecting thermal ablation of the endometrial lining tissue include circulation of heated fluid inside the uterus (either directly or inside a balloon placed in the uterus), laser treatment of the lining, and resistive heating using application of RF energy to the tissue to be ablated. Techniques using RF energy provide an RF electrical signal to one or more electrodes in contact with the subject organ tissue. Electrical current flows from the electrodes and into the organ tissue. The current flow resistively heats the surrounding tissue. Eventually, the heating process destroys the cells surrounding the electrodes and thereby effectuates ablation.

U.S. Pat. No. 6,508,815 (Strul et al.) and U.S. Pat. No. 6,813,520 (Truckai et al) describe a system and method for endometrial lining tissue ablation using an electrode carrying member to transmit radiofrequency (RF) energy to cause thermal heating and, thus, ablation of the tissue, wherein the electrode carrying member is substantially absorbent or permeable to moisture and gases such as steam, and is expandable to conform to the uterine cavity. A suction (aspiration) lumen is positioned within the electrode carrying member to aid in the removal of moisture, whether gas or liquid, present or generated during the ablation procedure. The electrode carrying member comprises an array of electrodes on its outer surface, the electrode array being configured for contacting the endometrial lining tissue in order to deliver energy sufficient to produce ablation to a predetermined depth. The electrode carrying member is collapsed and introduced into the uterine cavity, and then expanded within the uterine cavity so that the electrode array contacts the endometrial lining tissue to be ablated. An RF generator is used to deliver RF energy to the electrodes and to thereby induce current flow from the electrodes through the endometrial lining tissue. As the current passes through and heats the endometrial lining tissue, moisture (such as steam or liquid) leaves the tissue causing the tissue to dehydrate. However, the moisture permeability or absorbency of the electrode carrying member allows for moisture to leave the ablation site through an aspiration lumen of the ablation device to a waste collection receptacle located external to the patient, so as to prevent the moisture from providing a path of conductivity for the current that bypasses (i.e., short-circuits) the conductive pathway through the tissue.

The systems, devices and methods disclosed and described in U.S. Pat. Nos. 6,508,815 and 6,813,520 are well-suited for performing endometrial tissue ablation procedures, e.g., for treating Menorrhagia, the medical term for excessively heavy menstrual bleeding, and are embodied in the NovaSure® endometrial ablation system manufactured and distributed by Hologic, Inc., based in Bedford, Mass. U.S. Pat. Nos. 6,508,815 and 6,813,520 are hereby fully incorporated by reference.

U.S. Pat. Pub. No. 2011/0118718 also describes a system and method for endometrial RF ablation. This system uses an energy delivery device having a dielectric wall capable of non-expanded and expanded shapes, and having an indicator mechanism operatively coupled to the dielectric wall to indicate a dimension of the uterine wall. U.S. Pat. Pub. No. 2011/0118718 is hereby fully incorporated by reference.

FIGS. 1A-B illustrate an exemplary Novasure® endometrial ablation system 100. The ablation system 100 includes an expandable RF applicator head (electrode carrying member) 102, an introducer sheath 104, an introducer tubing 108, and a handle 106. The RF applicator head 102 is collapsed and slidably disposed within the introducer sheath 104 during insertion of the device into the uterine cavity via the introducer tubing 108 (FIG. 1A). The distal end of the sheath 104 is positioned within the uterus, and the handle 106 is manipulated to extend the RF applicator head 102 out an open distal end of the sheath 104 (FIG. 1B), and to expand the RF applicator head to conform to the uterine cavity (FIG. 2). As best seen in FIG. 2, the RF applicator head 102 includes a moisture permeable (woven) mesh electrode array 102a, and an underlying deflecting (i.e., expanding) mechanism 102b used to expand and tension the mesh electrode array 102a within the uterine cavity to facilitate contact between the endometrial lining tissue and the mesh electrode array 102a. The deflecting mechanism 102b includes a pair of metal ribbon flexures 124 extending distally and laterally out the introducer tubing 108 on opposite sides of a co-axially disposed pair of hypotubes 120 and 122 that also extend from tube 108. Non-conductive threads 148 extend from the inner hypotube 122 and have distal ends attached to internal flexures 136 that extend laterally and longitudinally from the exterior surface of hypotube 122.

As seen in FIG. 3A, a respective plurality of longitudinally spaced apart apertures 126 are formed in each flexure 124, which allow moisture in the uterine cavity to pass through the flexures and be drawn into the open distal end of the outer hypotube 120 by a vacuum source 552 fluidly coupled to the inner lumen of the hypotube 120. As seen in FIG. 3B, each flexure 124 includes conductive regions formed by isolated strips of metallic (e.g., copper) tape 128 that are electrically coupled to the array 102a for delivery of RF energy to the endometrial lining tissue. Anode and cathode conductors (not shown) are electrically coupled to respective ones of the strips 128, and extend through the tubing 108 (seen in FIG. 2) to an electrical cord 130, which may be operatively connected to an RF generator 550 (seen in FIG. 1A). During use, one strip 128 on each conductor is electrically coupled via the conductor leads to one terminal on the RF generator while the other strip is electrically coupled to the opposite terminal, thus causing the electrode array 102a on the applicator head 102 to have regions of alternating positive and negative polarity. Since it is important to have proper alignment and electrical contact between the conductive regions of the flexures 124 (e.g., copper strips 128) and electrodes 118a-118d (FIGS. 4A-B) strands of thread 134 (e.g., nylon) (FIG. 2) are sewn through the array 102a and around the flexures 124 in order to prevent the conductive regions 128 from slipping out of alignment with the electrodes 118a-118d.

Referring back to FIG. 2, each internal flexure 136 is connected at its distal end to one of the flexures 124, the deflecting mechanism further including a transverse ribbon 138 that extends between the distal portions of the internal flexures 136. The transverse ribbon 138 is preferably preshaped such that when in the relaxed condition the ribbon assumes the corrugated configuration and such that when in a compressed condition it is folded along the plurality of creases 140 that extend along its length. Flexures 124 and 136, and ribbon 138, are preferably made of an insulated spring material, such as heat treated 17-7 PH stainless steel.

Turning to FIGS. 4A-B, the electrode array 102a further includes a pair of broad faces 112 spaced apart from one another when the array 102a is expanded and tensioned by the deflecting mechanism 102b (FIGS. 2, 3A and 4A). The entire applicator head 102 is preferably coated with a dielectric material coating, such as parylene. Narrower side faces 114 extend between the broad faces 112 along the sides of the applicator head 102, and a distal face 116 extends between the broad faces 112 at the distal end of the applicator head 102. Insulating regions 110 are formed on the applicator head to divide the mesh into four electrodes 118a-118d by creating two electrodes on each of the broad faces 112. To create this four-electrode pattern, insulating regions 110 are placed longitudinally along each of the broad faces 112 as well as along the length of each of the faces 114, 116.

During use of the ablation system 100, distal and proximal grips 142 and 144 forming the handle 106 are squeezed towards one another to withdraw sheath 104 and deploy the applicator head 102 (FIG. 1B). This action results in relative rearward motion of the outer hypotube 120 and relative forward motion of the inner hypotube 122, causing deflection of flexures 124 and 136, thereby expanding and tensioning the electrode array 102a (FIG. 2). The deflecting mechanism 102b formed by flexures 124, 136, and ribbon 138, deploys the electrode array 102a into a uterine shape. Although the ribbon 138 of the deflecting mechanism 102b further maintains electrodes 118a-118d separated and insulated from each other during use of the system 100, the ribbon 138 is usually not adapted to further assist the distal face 116 of the electrode array 102a to contact a uterine fundus.

Accordingly, it would be desirable to provide for a simple deflecting mechanism for maintaining contact of the electrodes with the uterine fundus. Additionally, where expensive materials are used (e.g., materials of the flexures), or expensive or complex manufacturing techniques (e.g., deflecting mechanism and handle), it would be desirable to limit the quantity of these materials or complex manufacturing techniques, and provide for an ablation system as inexpensive and simple to manufacture as possible, while being well-suited for performing endometrial tissue ablation procedures.

SUMMARY

In accordance with various embodiments of the disclosed inventions, an endometrial tissue treatment device includes an elongate positioning member; and an energy applicator coupled to a distal end of the positioning member. The energy applicator includes a tissue contacting member (e.g., a moisture permeable energy delivery member), and an expandable-collapsible support structure underlying the tissue contacting member, the support structure including a substantially non-compliant elongate balloon that, when inflated, has a length oriented substantially transverse to the positioning member, including a first closed end that positions a corresponding first corner portion of the tissue contacting member in a first cornu of a uterine cavity, and a second closed end that positions a corresponding second corner portion of the tissue contacting member in a second cornu of the uterine cavity, with a lengthwise portion of the balloon positioning a distal facing portion of the tissue contacting member for contacting a fundal wall of a uterus.

In one such embodiment, the endometrial tissue treatment device further includes an elongate hollow delivery sheath having a distal portion configured for transcervical placement into a uterus, the delivery sheath having a lumen and an open distal end in communication with the lumen, wherein the respective positioning member and energy applicator are slidably disposed in the delivery sheath lumen so that the energy applicator slidably moves between a collapsed configuration in which the energy applicator is at least partially withdrawn through the open distal end of the delivery sheath and into the delivery sheath lumen, and an extended configuration in which the energy applicator is extended out the open distal end of the delivery sheath and at least partially self-expanded to conform to a uterine cavity. The delivery sheath and positioning member may be operatively coupled to an actuator that moves the positioning member relative to the delivery sheath to thereby move the energy applicator between the collapsed configuration and the extended configuration. For example, the actuator can be a grip-style handle that is actuated by squeezing together a pair of pivotably connected grip members.

The endometrial tissue treatment device has at least one inflation member (e.g., a flexible plastic tubing) having an inflation lumen fluidly coupled to an interior of the balloon, with a proximal end of the respective inflation member configured for fluidly coupling the respective inflation lumen with a source of inflation media, e.g., a syringe that can also be used to deflate the balloon after use of the device. In various embodiments, an aspiration lumen extends through the positioning member, having an open distal end located within the support structure of the energy applicator when the energy applicator is in the extended configuration.

In some embodiments, the treatment device further includes an elongate tensioning member that is movable relative to the positioning member, the tensioning member having a distal end fixed to the balloon at an approximate lengthwise midpoint of the balloon. By way of non-limiting example, the distal end of the tensioning member comprises or is connected to a ring member that at least partially circumferentially surrounds the balloon at the approximate lengthwise midpoint of the balloon.

In some embodiments, the expandable-collapsible support structure further comprises opposing first and second flexures disposed within the tissue contacting member, the flexures having a delivery configuration in which the flexures are in a side-by-side configuration aligned with the positioning member, and a deployed configuration in which a distal end of the first flexure is positioned in the first corner portion of the tissue contacting member, and a distal end of the second flexure is positioned in the second corner portion of the tissue contacting member, the first and second flexures having arcuate outer surfaces. Further, in the side-by-side delivery configuration, the arcuate outer surfaces of the first and second flexures together define a cylindrical outer surface. Also, in the side-by-side delivery configuration, the distal ends of the first and second flexures together define a tapered or rounded tip. In these embodiments, the first and second flexures each comprise one or more embedded conductors, each conductor electrically connected to a respective portion of the tissue contacting member. At least one of the first and second flexures comprises an embedded inflation lumen fluidly coupled to an interior of the balloon.

In one embodiment, an endometrial lining tissue treatment device includes an elongate hollow delivery sheath having a distal portion configured for transcervical placement into a uterus, the delivery sheath having an axial lumen and an open distal end in communication with the lumen, an elongate positioning member slidably disposed in the delivery sheath lumen, and an energy applicator coupled to a distal end of the positioning member, wherein movement of the positioning member distally relative to the delivery sheath, or of the delivery sheath proximally relative to the positioning member, moves the energy applicator from a collapsed configuration in which the energy applicator is at least partially withdrawn through the open distal end of the delivery sheath and into the delivery sheath lumen, to an extended configuration in which the RF applicator is extended out the open distal end of the delivery sheath and at least partially self-expanded to substantially conform to a uterine cavity. The delivery sheath and positioning member may be operatively coupled to an actuator that moves the positioning member relative to the delivery sheath to thereby move the energy applicator between the collapsed configuration and the extended configuration.

The energy applicator includes a tissue contacting energy delivery member and an expandable-collapsible support structure underlying the energy delivery member, the expandable-collapsible support structure comprising a substantially non-compliant elongate balloon that, when inflated with the energy applicator in the extended configuration, has a length oriented substantially transverse to the positioning member, including a first closed end that positions a corresponding first corner portion of the energy delivery member in a first cornu of a uterine cavity, and a second closed end that positions a corresponding second corner portion of the energy delivery member in a second cornu of a uterine cavity. The device further includes at least one inflation member having an inflation lumen fluidly coupled to an interior of the balloon, with a proximal end of the respective inflation member configured for fluidly coupling the respective inflation lumen with a source of inflation media.

The energy delivery member may be moisture permeable, and the device may further include an aspiration lumen extending through the positioning member and having an open distal end located within the support structure of the energy applicator when the energy applicator is in the extended configuration. The delivery sheath and positioning member may be operatively coupled to an actuator that moves the positioning member relative to the delivery sheath to thereby move the energy applicator between the collapsed configuration and the extended configuration, the actuator comprising a grip-style handle that is actuated by squeezing together a pair of pivotably connected grip members. The device may further include an elongate tensioning member that is movable relative to the positioning member, the tensioning member having a distal end fixed to the balloon at an approximate lengthwise midpoint of the balloon. By way of example, a distal end of the tensioning member may comprise or otherwise be connected to a ring member that at least partially circumferentially surrounds the balloon at the approximate lengthwise midpoint of the balloon.

An endometrial tissue treatment device constructed according to yet another embodiment includes an elongate positioning member, an energy applicator coupled to a distal end of the positioning member, the energy applicator including an tissue contacting member and an expandable-collapsible support structure underlying the tissue contacting member, the expandable-collapsible support structure comprising a substantially non-compliant elongate balloon that, when inflated, has a length oriented substantially transverse to the positioning member, including a first closed end that positions a corresponding first corner portion of the tissue contacting member in a first cornu of a uterine cavity, and a second closed end that positions a corresponding second corner portion of the tissue contacting member in a second cornu of a uterine cavity, with a lengthwise portion of the balloon positioning a distal facing portion of the tissue contacting member for contacting a fundal wall of a uterus. The device includes at least one inflation member having an inflation lumen fluidly coupled to an interior of the balloon, with a proximal end of the respective inflation member configured for fluidly coupling the respective inflation lumen with a source of inflation media. The device may further include an elongate tensioning member that is movable relative to the positioning member, the tensioning member having a distal end fixed to the balloon at an approximate lengthwise midpoint of the balloon.

The device of this embodiment may further include an elongate hollow delivery sheath having a distal portion configured for transcervical placement into a uterus, the delivery sheath having a lumen and an open distal end in communication with the lumen, wherein the respective positioning member and energy applicator are slidably disposed in the delivery sheath lumen so that the energy applicator slidably moves between a collapsed configuration in which the energy applicator is at least partially withdrawn through the open distal end of the delivery sheath and into the delivery sheath lumen, and an extended configuration in which the energy applicator is extended out the open distal end of the delivery sheath and at least partially self-expanded to conform to a uterine cavity, wherein the delivery sheath and positioning member are operatively coupled to an actuator that moves the positioning member relative to the delivery sheath to thereby move the energy applicator between the collapsed configuration and the extended configuration.

Other and further aspects and features of embodiments of the disclosed inventions will become apparent from the ensuing detailed description in view of the accompanying figures.

BRIEF DESCRIPTION OF THE DRAWINGS

FIG. 2 is a cross-sectional view of the conventional (Prior Art) ablation system distal end of FIGS. 1A-B;

FIGS. 3A-B are perspective and cross-sectional views of the conventional (Prior Art) deflecting mechanism of the ablation system of FIGS. 1A-B;

FIG. 10 is a cross-sectional view of an ablation system constructed according to another embodiment of the disclosed inventions; and FIG. 11A-B are cross-sectional views depicting a deflecting mechanism of the ablation system of FIG. 10.

DETAILED DESCRIPTION OF THE ILLUSTRATED EMBODIMENTS

Figure 1A:
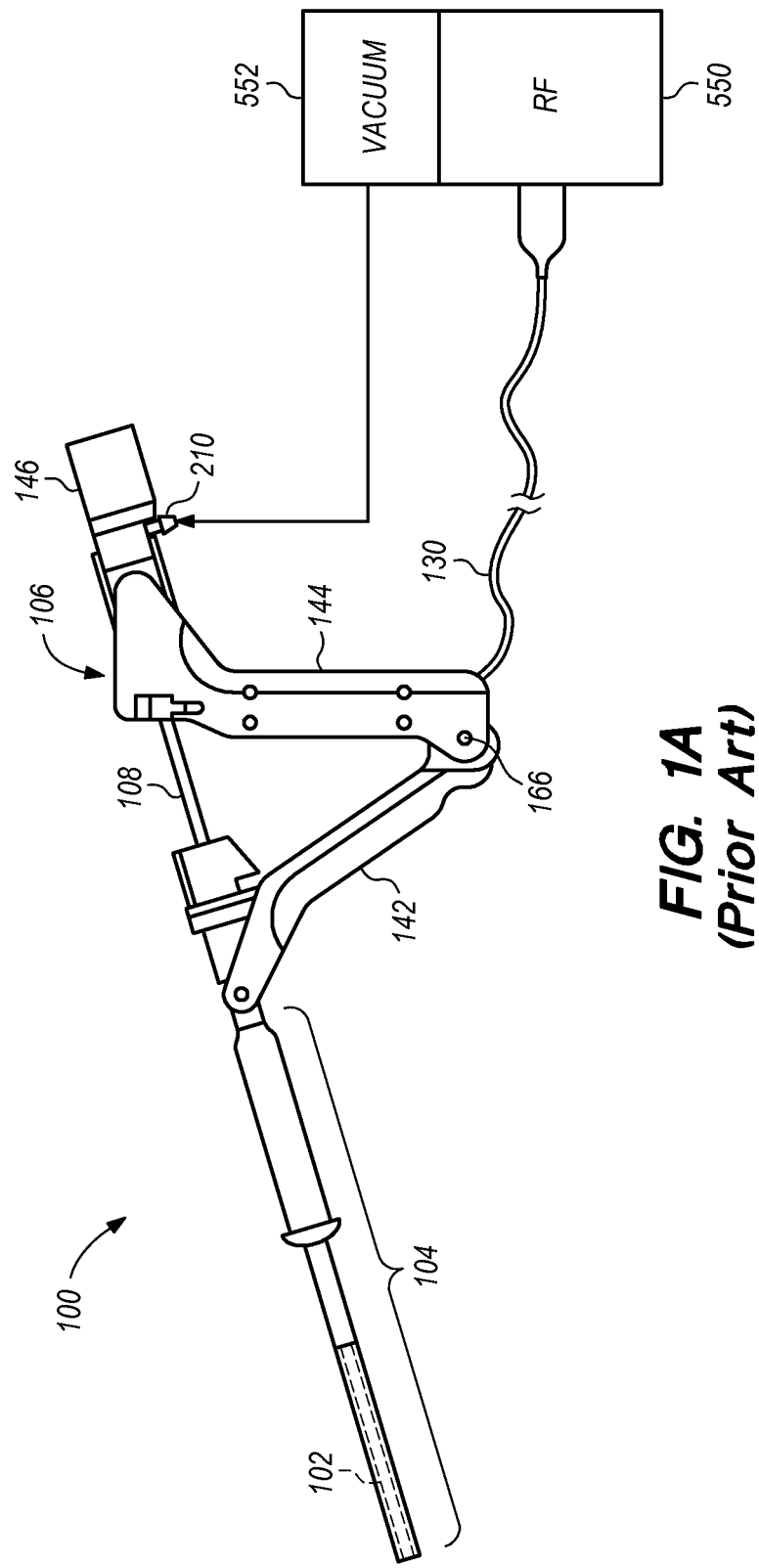
FIGS. 1A-B are perspective views of a conventional (Prior Art) ablation system.
Figure 1B:
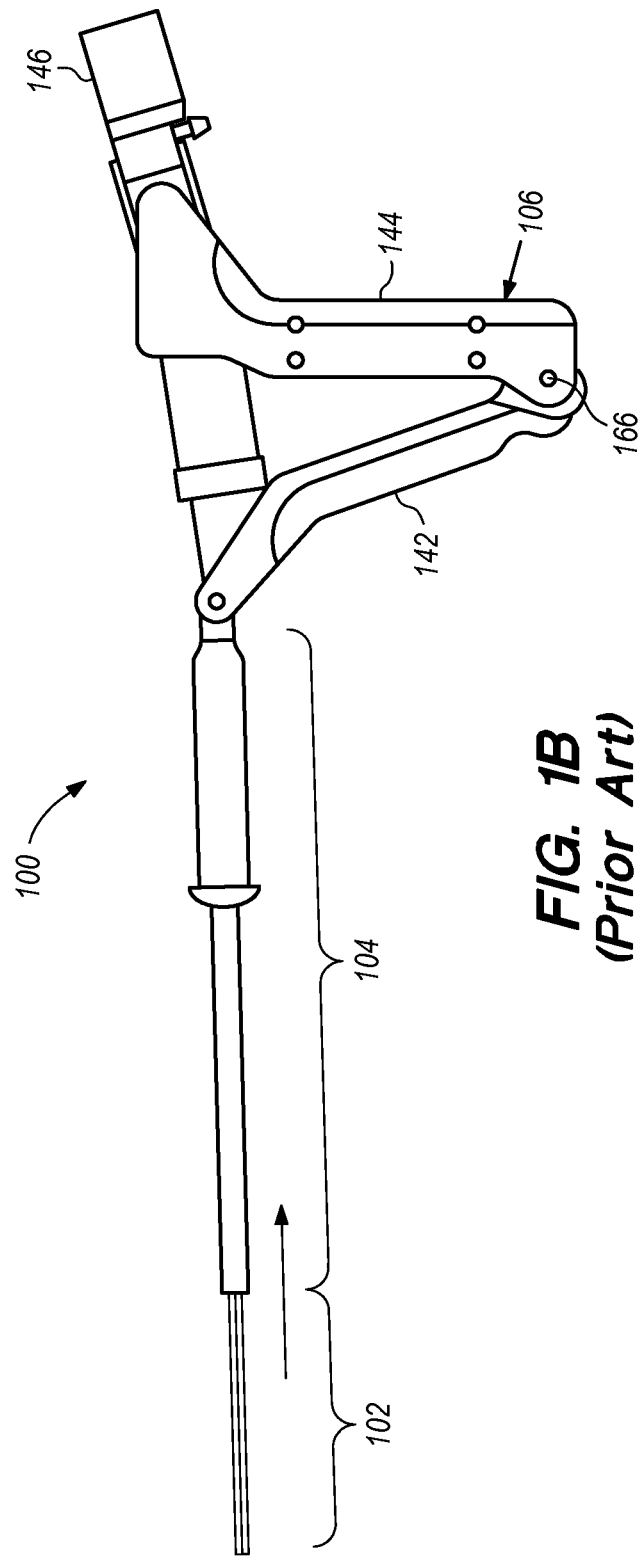

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 5:
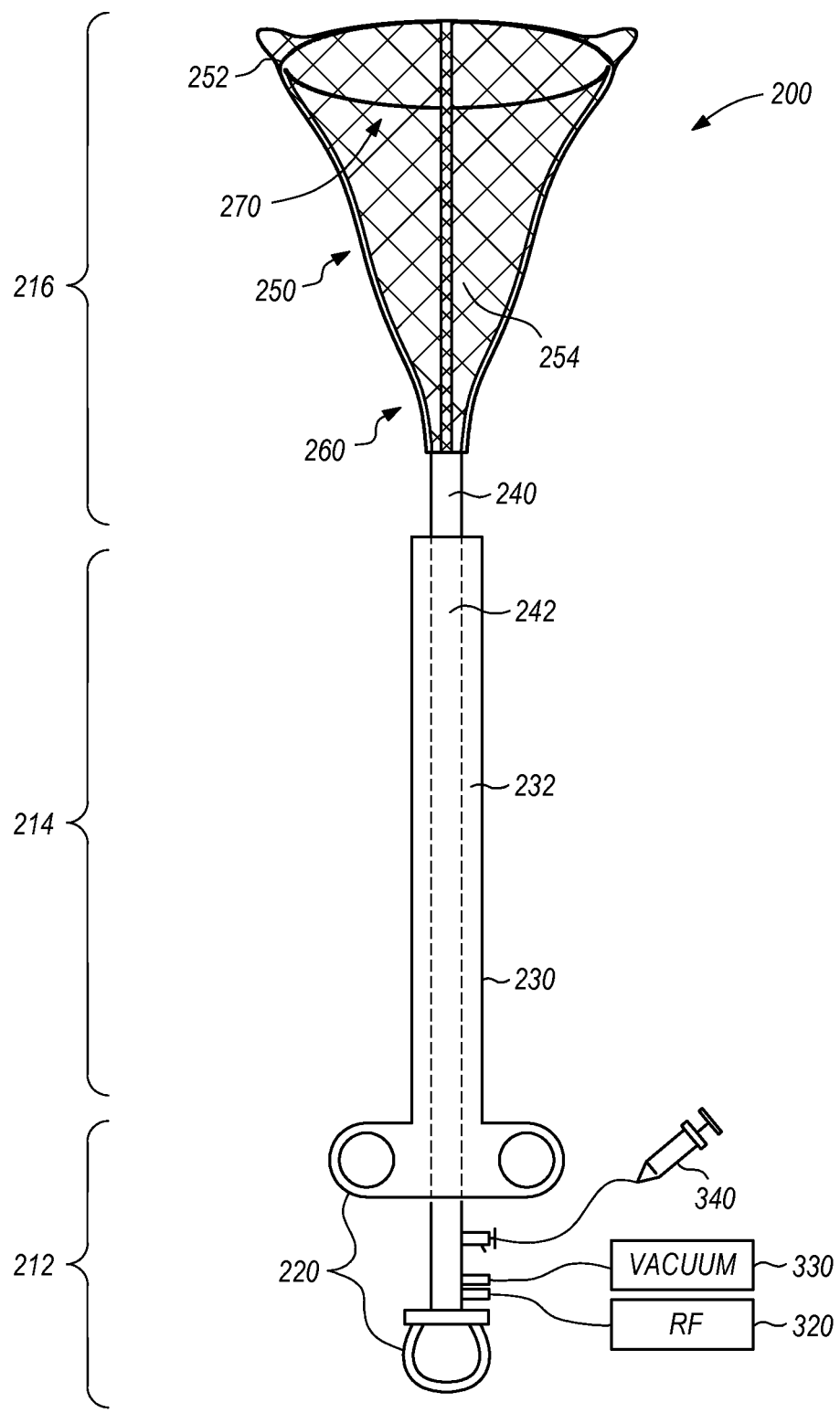
FIG. 5 is a cross-sectional view of an ablation system constructed according to one embodiment of the disclosed inventions.

FIG. 5 is a medical ablation system 200 for RF energy delivery into a target site (e.g., a uterus) of a patient, constructed in accordance with a one embodiment of the disclosed inventions. The ablation system 200 includes a proximal portion 212, a middle portion 214, and a distal portion 216. The proximal portion 212 includes a handle 220 for controlling and manipulating the medical ablation system 200, which will be described in more detail below. The middle portion 214 of the ablation system 200 includes an outer elongate member 230 having an axially lumen 232, and an inner elongate member 240 having an axial lumen 242. The inner elongate member 240 is coaxially disposed within the axial lumen 232 of the outer elongate member 230, with the outer elongate member 230 being slidable relative to the inner elongate member 240 by manipulation of the handle 220.

The distal portion 216 of the ablation system 200 includes an energy delivery member 250. The energy delivery member 250 comprises an outer surface 252 having an electrode array 260, and an interior cavity 254 in which an inflatable deflecting mechanism 270 is positioned. The electrode array 260 may be coupled to an RF source 320 that generates and provides energy (i.e., RF current) to the electrode array 260 via one or more conductors extending through the device to an electrical connector in the handle 220. During operation of the device, the interior cavity 254 of the energy delivery member 250 is placed in fluid communication with a vacuum source 330 via lumen 242 of the inner member 240 coupled to an aspiration port in the handle 220.

The ablation system 200 has a delivery configuration (FIGS. 8A and 9A) in which the energy delivery member 250 is in a radially collapsed configuration constrained by the outer elongate member 230, and the deflecting mechanism 270 is deflated (FIGS. 7A and 7C), and a deployed configuration (FIGS. 8-C and 9B-C) in which the energy delivery member 250 is in a radially expanded configuration when the outer elongate member 230 is withdrawn, and in which the deflecting mechanism 270 is inflated (FIGS. 7B and 7D), as is described in more detail below. In an alternative embodiment, the ablation system 200 does not include the outer elongate member 230 (i.e., member/sheath 230 is optional) to radially collapse the energy delivery member 250 and deflecting mechanism 270; other suitable means can be used to achieve the deployed and/or collapsed configuration of the ablation system 200, such as a vacuum.

Figure 6:
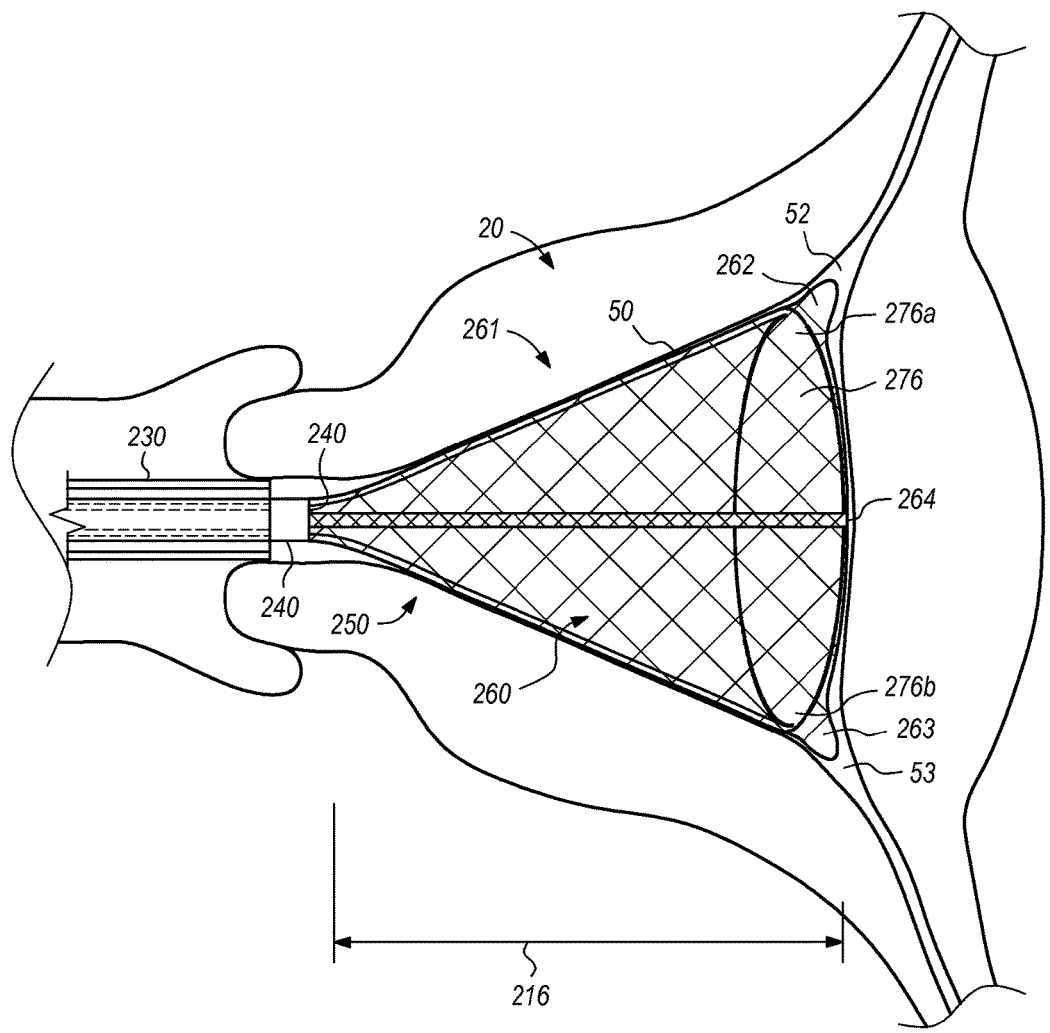
FIG. 6 is a perspective view an exemplary energy delivery member and a deflecting mechanism construction according to one embodiment of the disclosed inventions.

FIG. 6 illustrates the distal portion 216 of the ablation system 200 in a deployed configuration, as constructed according to one embodiment of the disclosed inventions. The endometrial ablation system 200 includes the inner elongate positioning member 240 and the energy applicator 261 coupled to a distal end 241 of the inner elongate positioning member 240. The energy applicator 261 of the endometrial ablation system 200 comprises a tissue contacting member (i.e., electrode array 260) and an expandable-collapsible support structure (i.e., deflecting mechanism 270 shown in FIGS. 8A-8C) underlying the tissue contacting member. The expandable-collapsible support structure comprises a substantially non-compliant elongate balloon 276 disposed within the tissue contacting member 260 that, when inflated, has a length oriented substantially transverse to the inner elongate positioning member 240, including a first closed end 276a that positions a corresponding first corner portion 262 of the tissue contacting member 260 in a first cornu 52 of a uterine cavity 50, and a second closed end 276b that positions a corresponding second corner portion 263 of the tissue contacting member 260 in a second cornu 53 of a uterine cavity 50 of a uterus 20.

Figure 4A:
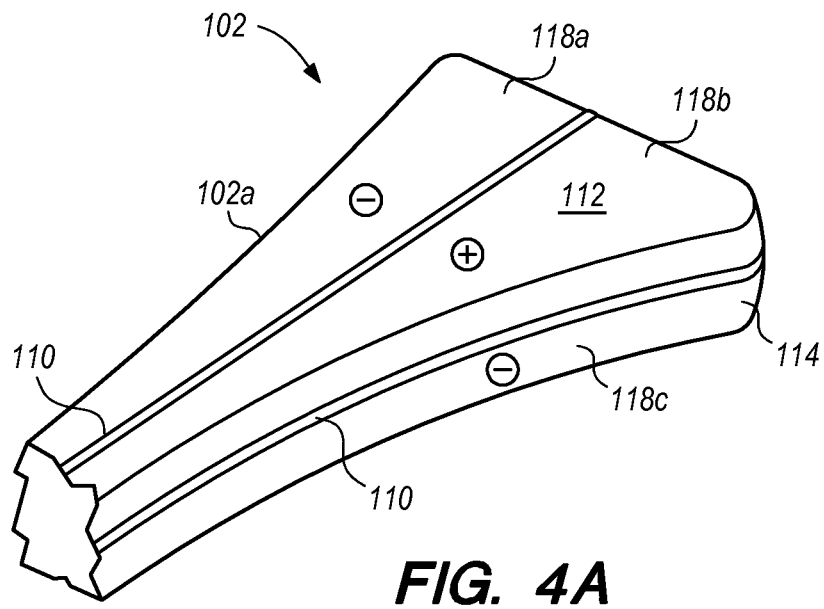
FIGS. 4A-B are perspective and cross-sectional views of the conventional (Prior Art) electrode array of the ablation system of FIGS. 1A-B.
Figure 4B:
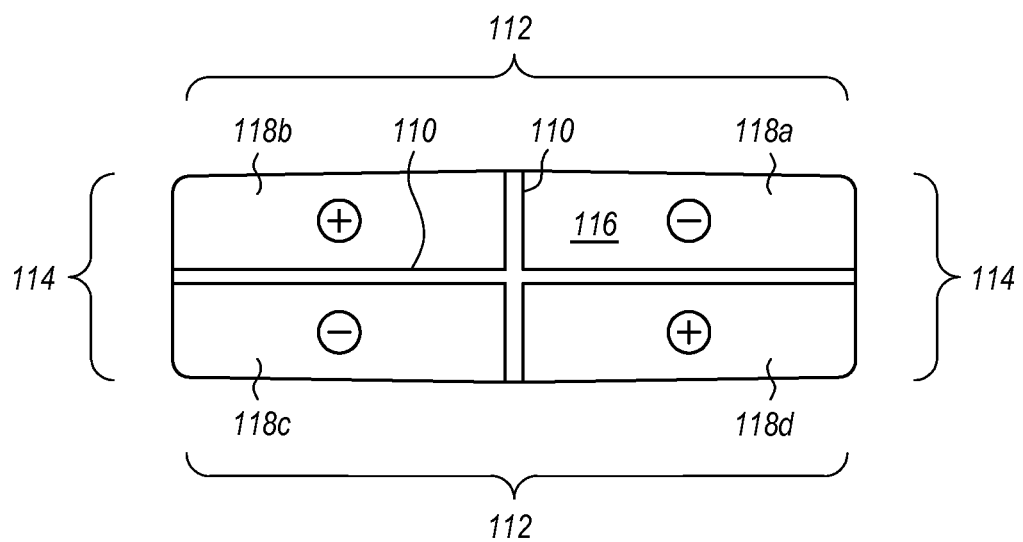

The ablation system 200 has an expandable energy delivery member 250 including an electrode array 260 formed of a stretchable electrically conductive mesh. In a preferred embodiment, the electrode array 260 is formed from a braided mesh of elastic (e.g., spandex) and relative inelastic (e.g., nylon) yarns plated with gold or other conductive material. The braid of elastic and inelastic yarns allows for a pre-determined overall deformability of the electrode array 260. Further, the elastic yarns provide the needed elasticity to the electrode array 260 for deployment, while the inelastic yarns provide relatively non-stretchable members so that gold or other conductive metals and materials can be plated, coated, adhered or carried without cracking or breaking during expansion of the electrode array 260. In one embodiment, the electrode array 260 may be configured the same or similarly to the prior art electrode array 102a depicted in FIGS. 4A-B, such as having four electrodes with insulating regions 264.

FIGS. 7A-D illustrate a deflecting mechanism 270 of the ablation system 200, constructed according to one embodiment of the disclosed inventions. The deflecting mechanism 270 includes first and second elongate tubular inflation/support members 272 coupled at respective transverse ends of an inflatable deflecting balloon 276. Each elongate tubular member 272 has an inner lumen 274 in fluid communication with an interior of the balloon 276 for supplying a fluid and/or gas source for selected inflation of the balloon 276. For example, the fluid/gas source may be a syringe, such as syringe 340 depicted in FIG. 5, filled with a predetermined volume of fluid or gas to adequately inflate the deflecting balloon 276. Reverse action of the syringe 340 could similarly be used to deflate the deflecting balloon 276 by withdrawing the fluid/gas from the balloon 276 back into the syringe 340. The fluid/gas source 340 may optionally include a pressure sensor to measure the inflation pressure to ensure adequate inflation without over inflation of the deflecting balloon 276. It will be appreciated that in an alternative embodiment, only a single inflation member/lumen 274/272 may be used to inflate (and deflate) the deflecting balloon 276. Alternatively, the deflecting mechanism may be constructed similar to applicator head 102, shown in FIGS. 2 and 3A, except that transverse ribbon 138 is replaced with balloon 276 and flexures 124 made from metal or PEEK.

Figure 7A:
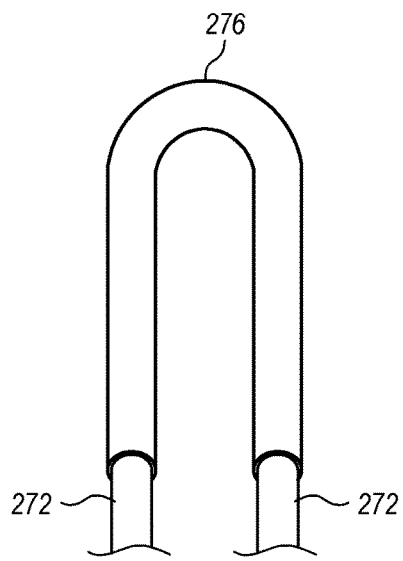
FIGS. 7A-D are perspective views of deflecting mechanisms constructed according to additional and alternative embodiments of the disclosed inventions.
Figure 7B:
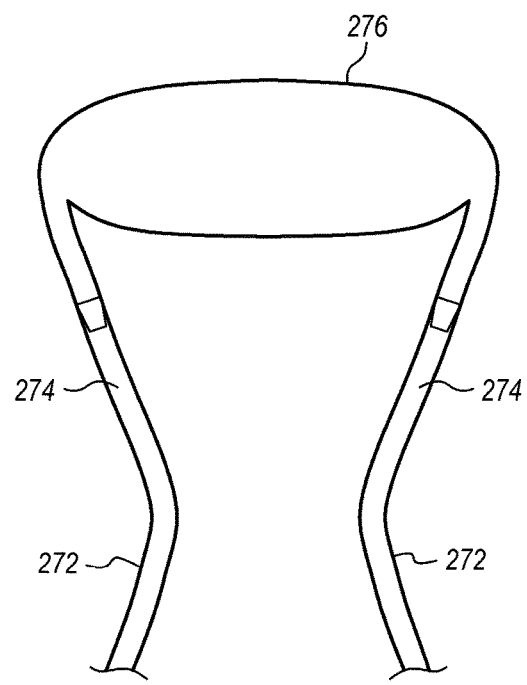
Figure 7C:
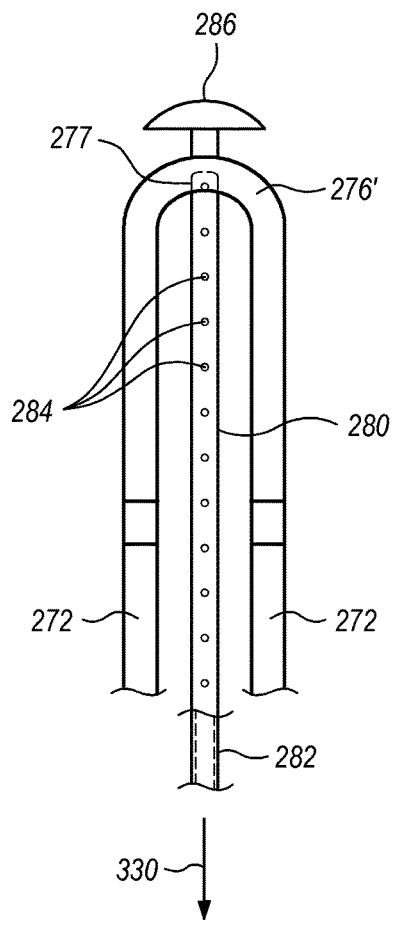
Figure 7D:
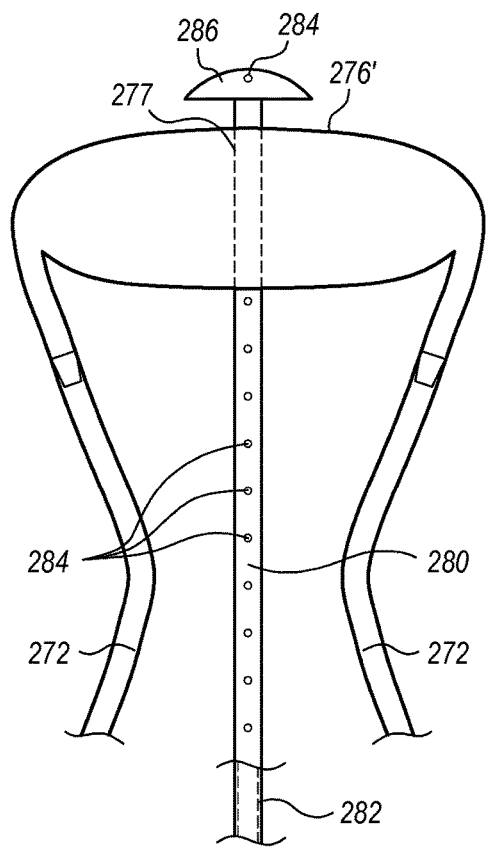
Figure 7E:
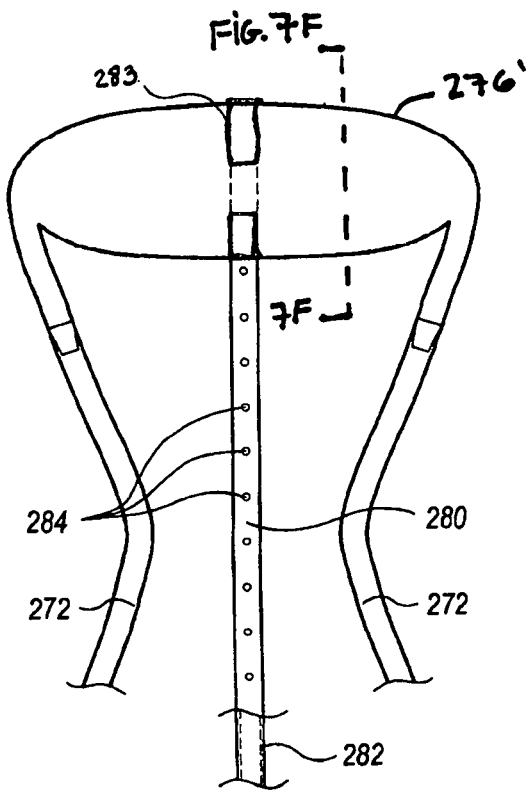
FIG. 7E is a perspective view of an alternate deflecting mechanism in which a tensioning member is connected to a ring member that at least partially circumferentially surrounds the balloon.
Figure 7F:
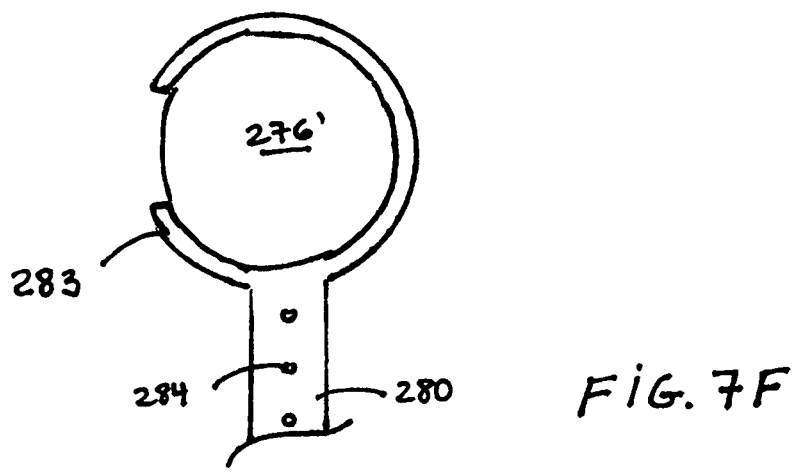
FIG. 7F is a cross-sectional end view taken along lines 7F-7F in FIG. 7E.

As shown in FIGS. 7E and 7F, in a further alternate embodiment, the distal end of a tensioning member 280 comprises or is otherwise connected to, a ring member 283 that at least partially circumferentially surrounds the deflecting balloon 276' at the approximate lengthwise midpoint of the balloon 276'. Again, only a single inflation member/lumen 284/282 may be used to inflate (and deflate) the deflecting balloon 276'.

Figure 8A:
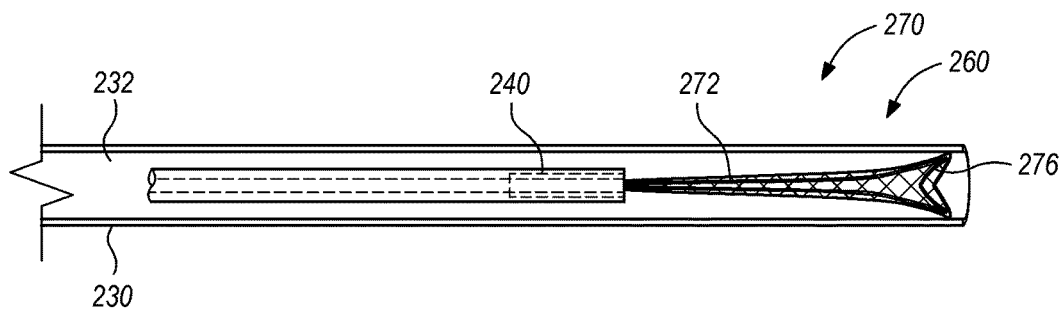
FIGS. 8A-C are cross-sectional views depicting a method of deployment of the energy delivery member using the ablation system of FIG. 5, and the deflecting mechanism of FIGS. 7A-B.
Figure 8C:
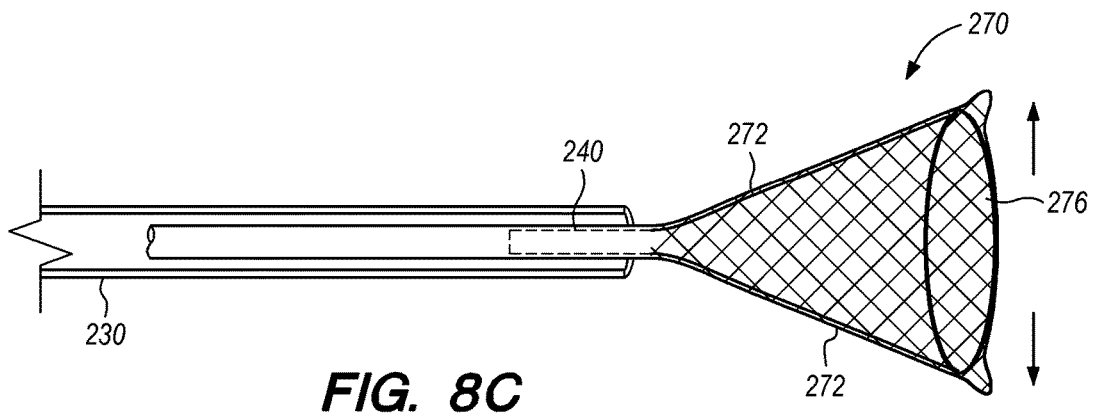
Figure 9A:
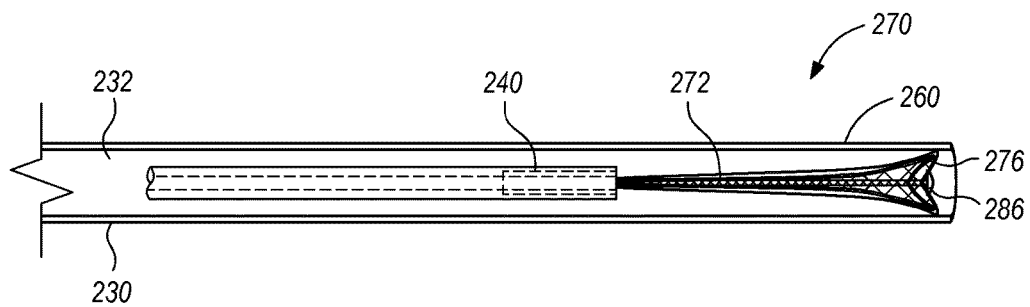
FIGS. 9A-C are cross-sectional views depicting a method of deployment of the energy delivery member using the deflecting mechanism of FIGS. 7C-D.

When the deflecting mechanism 270 is disengaged, the deflecting balloon 276 is deflated (FIGS. 7A and 7C), so that the energy delivery member 250 of the ablation system 200 is in the delivery configuration (FIGS. 8A and 9A). When the deflecting mechanism 270 is engaged, the deflecting balloon 276 is inflated (FIGS. 7B and 7D) expanding the energy delivery member 250 into the deployed configuration (FIGS. 5, 6, 8C, and 9C). The deflecting balloon 276, when inflated, causes expansion and tensioning of the array electrode 260 for positioning into contact with tissue (e.g., endometrium), and further allows atraumatic contact of the distal region of the electrode array 260 with tissue, e.g., the uterine fundus.

The elongate members 272 may be made of polymeric materials, metals and/or alloy materials, such as polyethylene, polyether ether ketone (PEEK), stainless-steel (e.g., 17-7PH), or other suitable biocompatible materials or combinations thereof. The deflecting balloon 276 may be made of or otherwise include polymeric materials, such as silicone, urethane polymer, thermoplastic elastomer rubber, santoprene, nylon, polyethylene terephthalate (PET), and other suitable materials or combinations thereof.

In a preferred embodiment, the deflecting balloon 276 is composed of a noncompliant material, such as polyurethane terephthalate (PET), which allows and facilitates inflation of the balloon with the syringe 340 filled with a predetermined volume of fluid (e.g., air). The predetermined volume of fluid may correspond to, for example, a preformed volume of balloon 276. Having the syringe 340 filled with a predetermined volume of fluid to inflate the noncompliant material balloon 276 reduces the risk of overinflating and overextending of the balloon 276 in its deployed configuration. The balloon 276 may be manufactured with standard processing equipment to obtain a balloon having a wall thickness of approximately between 0.0005 inches to 0.005 inches, in a deflated configuration. The deflecting balloon 276 is manufactured to comprise an elongate, cylindrical, and/or tubular configuration (e.g., FIGS. 5-9C). Alternatively, the deflecting balloon 276 may be manufactured to comprise any other suitable configuration. For example, the deflecting balloon 276 may comprise a plurality of bellows or accordion-like configuration (not shown).

Additionally, the deflecting balloon 276 composed of non-compliant material is configured to withstand higher inflation pressure without deforming or overextending, than balloons composed of compliant materials. In one embodiment, the deflecting balloon 276 composed of non-compliant material is inflated with air, which has little thermal capacity, so that the air-inflated deflecting balloon 276 will not draw significant thermal energy from the electrode array 260 when energy is delivered to ablate tissue. Further, the air-inflated deflecting balloon 276 composed of noncompliant material is configured to withstand temperatures about 100° C. during ablation procedures, minimizing the risk of bursting or failing of the balloon 276.

In an alternative embodiment, the deflecting balloon 276 may be filled with fluid (i.e., saline), so that the balloon 276 may act as a cooling element drawing thermal energy away from the tissue when energy is delivered by the electrode array 260. It would be understood, that the energy drawn by the balloon filled with fluid, would be taken into consideration by the designer/manufacturer of system 200 and/or by the attending physician or technician during a procedure to determine a proper tissue ablation depth.

Alternatively, the deflecting mechanism 270 may be slideably coupled to a central elongate member 280 to facilitate uniform deployment regardless of uterus width. Additionally, the central elongate member 280 may comprise an actuation mechanism, such as a spring, coil or any other suitable mechanism (not shown) to further assist with the deployment of the deflecting mechanism 270 (e.g., distally translating or pushing the balloon 276). The central elongate member 280 has a lumen 282 and a plurality of apertures 284 fluidly coupled to the vacuum source 330 (FIGS. 7C-D), so that during the ablation procedure, steam, blood and other fluids are suctioned and removed from a body organ. The central elongate member 280 may be slidably coupled to deflecting balloon 276' so that central elongate member 280 can move relative to deflecting balloon 276' in a direction transverse to the other. The central elongate member 280 further includes a non-traumatic distal bumper 286. The distal bumper 286 may include one or more apertures 284 (not shown) fluidly coupled to the vacuum source 330, so that during the ablation procedure, steam, blood and other fluids are suctioned and removed from a fundus or fundal wall. The deflecting balloon 276' has a passageway 277 for allowing passage and longitudinal movement of the central elongate member 280, while allowing the deflecting balloon 276' to be inflated and to maintain the inflated/deployed configuration (FIG. 7D). The passageway 277 of the deflecting balloon 276' may have an elongated, annular, or "donut hole" like configuration, allowing the central elongate member 280 to be slidably disposed within the passageway 277, so that when the deflecting balloon 276' is inflated and expands/deploys the electrode array 260 (e.g. outwardly) (FIGS. 9B-C), the central elongate member 280 is distally translated to further facilitate uniform deployment of the electrode array 260 (e.g. distally and/or outwardly) regardless of uterus width. In an alternative embodiment, two or more deflecting balloons 276 may be incorporated and/or used in the deflecting mechanism 270 (not shown), so that the pathways of the central elongate member 280 is defined between the two or more balloons, with no need for a passageway 277 formed in or within the deflecting balloons 276.

Figure 9B:
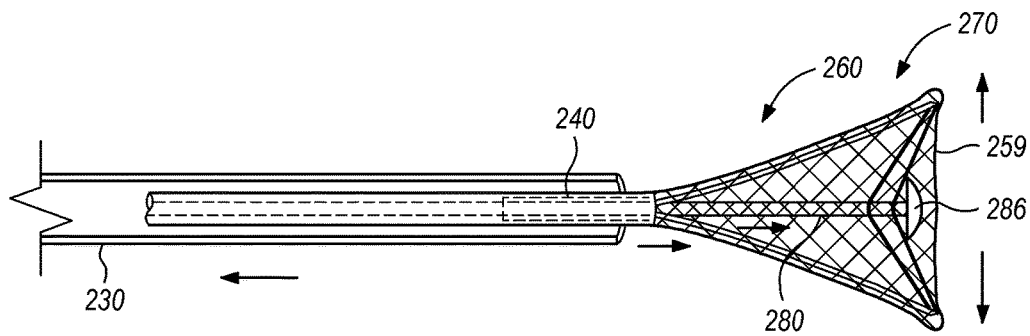
Figure 9C:
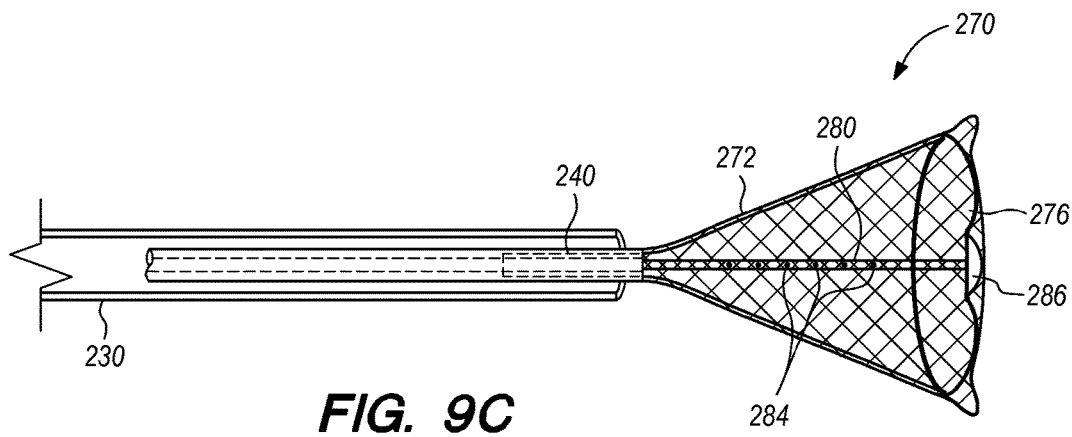

Alternatively, the central elongate member 280 may comprise a plurality of circumferentially disposed protrusions, annular protrusions and/or restriction knots (not shown) disposed proximal to the distal bumper 286, so that the deflecting balloon 276' is disposed between the proximal protrusion(s) and the distal bumper 286. The protrusion(s) may further facilitate uniform deployment of the electrode array 260 by pushing the inflated deflecting balloon 276' towards the distal surface 259 of the energy delivery member 250 (FIG. 9B-C). Additionally, it should be appreciated that the protrusion(s) of the central elongated member 280 (FIGS. 9A-C) and/or any suitable shaping members (not shown) of the ablation system 200 may further facilitate the distal portion 216 of the system 200 to form, mimic and/or conform to an uterine cavity shape, dimension and configuration, when the ablation system 200 transitions into the deployed configuration. Further, the central elongate member 280 may include a plurality of conductive strips (not shown) that are electrically coupled to the electrode array 260 for delivery of RF energy to the endometrial lining tissue. Alternatively, the plurality of conductive strips may be woven within the electrode array 260 (not shown). It should be appreciated that the woven conductive strips may be insulated (e.g., non-conductive coating) yet the strips are electrically coupled at some point of the strip to the electrode array 260.

Figure 8B:
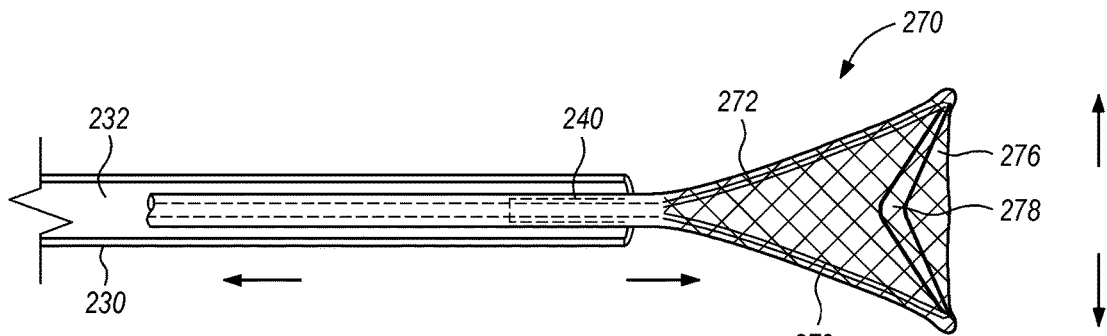

FIGS. 8A-C illustrate an exemplary method of deployment of the electrode array 260 using the deflecting mechanism 270 of FIGS. 7A-B. FIG. 8A depicts the distal portion 216 of the ablation system 200 disposed within the lumen 232 of the outer elongate member 230, having the electrode array 260 in a delivery configuration and the deflecting balloon 276 deflated. Concurrently or sequentially with relative movement of the outer elongate member 230 and the deflecting mechanism 270, the deflecting mechanism 270 is engaged by inflating the deflecting balloon 276 (FIG. 8B), thereby expanding the electrode array 260 into the deployed configuration (FIG. 8C). The deflecting balloon 276 includes a preferential fold 278 when deflated (FIGS. 8A-B) until the balloon 276 is fully inflated to substantially 100% of its preformed volume (FIG. 8C). The preferential fold 278 may comprise one or more pleat, bend, crease, crimp, or the like. The preferential fold 278 may be formed at the manufacturing stage of the deflecting balloon 276, assisting the deflecting balloon 276 to maintain an insertion profile (FIG. 8A). Alternatively, preferential fold 278 may be caused by disposing the ablation system 200 into the delivery configuration. In either embodiment, the preferential fold 278 would allow for a consistent inflation pattern of the deflecting balloon to be fully inflated, so that the ablation system 200 transitions into the deployed configuration (FIGS. 8B-C).

The inflated deflecting balloon 276 applies outward spreading force to the elongate members 272 and the electrode array 260 for deployment of the array. Additionally, the deflecting mechanism 270 including the inflated deflecting balloon 276 is configured to maintain the electrode regions separated to avoid contact between the electrodes, during the ablation procedure. The inflated deflecting balloon 276 applies an outward spreading force to the electrode array 260. The spreading force causes the array 260 to take on a shape similar to the uterine cavity whereby the distal region of the electrode array 260 contacts at least a portion of a uterine fundus before vacuum is applied.

FIGS. 9A-C illustrate an exemplary method of deployment of the electrode array 260 using the deflecting mechanism 270 of FIGS. 7C-D, in accordance with embodiments of the disclosed inventions. FIG. 9A illustrates the distal portion 216 of the ablation system 200 disposed within the lumen 232 of the outer elongate member 230, having the electrode array 260 in a delivery configuration including the central elongate member 280, and having the deflecting balloon 276' in a deflated delivery configuration. As shown in FIGS. 9B-C, the following acts occur: 1) the outer elongate member 230 is proximately withdrawn; 2) the central elongate member 280 is translated distally so that its distal bumper 286 contacts and pushes the distal surface 259 of the energy delivery member 250, assisting with the deployment of the electrode array 260, further allowing contact of the electrodes with a uterine fundus, and 3) the deflecting mechanism 270 is engaged and inflates the deflecting balloon '276 further expanding the electrode array 260 into the deployed configuration (FIG. 9C). As alternative acts 1) of FIG. 9B, the deflecting mechanism 270 is distally translated, or the distal translation of the deflecting mechanism 270 occurs simultaneously or consecutively to the proximal withdrawal of the outer elongate member 230.

In an alternative embodiment, the bumper 286 may be coupled, attached or secured to the distal surface 259 of the energy delivery member 250, so that the distal surface 259 is pushed/advanced when the central elongate member 280 is translated distally, and the distal surface 259 is pulled/withdrawn when the central elongate member 280 is translated proximately.

In an alternative embodiment, the outer elongate member 230 withdrawal may be coupled to the actuation of the syringe 340 providing simultaneous withdrawal of the outer elongate member 230, deflecting/actuation and inflation of the deflecting balloons 276 and 276' (FIGS. 8B-C and 9B-C).

In an alternate embodiment, a chemical agent may be used for ablating the endometrial ling tissue. Such a treatment system would be less expensive and less complicated to use than an RF (i.e., thermal) tissue ablation system. By way of example, a chemical ablation technique using a silver nitrate (AgNO3) paste shows promise for endometrial lining tissue ablations. Envisioned is an expandable uterine ablation head similar to the ones disclosed herein, except that the expandable ablation head is coated with a toxic chemical instead of carrying an electrode array. Such a device would allow for controlled ablation occurring only where the coated array is in direct contact with tissue. To coat the ablation head with silver nitrate, the silver nitrate is first mixed with polyvinyl alcohol (PVA) and de-ionized (DI) water. PVA is a water soluble polymer used for controlled drug delivery. By controlling quantity of PVA and silver nitrate, the depth and duration of the ablation can be controlled.

For example, the external surface material of the expandable ablation head may be dip coated with a silver nitrate/PVA mixture in production before curing. In an alternative embodiment, the silver nitrate/PVA mixture could be applied to specific regions or sides of the array to provide a more local ablation or maintain an area of un-ablated endometrial lining to prevent adhesions. In another alternative embodiment, the chemical used to cause the ablation could be gold chloride. Although more costly than silver nitrate, gold chloride may provide for a more rapid ablation. Water soluble polymers could alternatively be used for bonding the ablation chemical to the array.

The chemical ablation device may incorporate features of NovaSure RF system not specific to electrical energy delivery, including cavity integrity assessment (CIA), vacuum, and variable length and width. Deployment of the ablation head within the uterus array may be achieved with a mechanical tensioning mechanism, such as the balloon actuator disclosed and described herein, or an assembly of metallic flexures, such as used in the NovaSure system.

FIG. 10 illustrates an alternative embodiment of a medical ablation system 200' for RF energy delivery into a target site (e.g., a uterus) of a patient, constructed in accordance with the disclosed inventions. For ease in illustration and disclosure, the features and configurations of the ablation system 200' that are the same as the ablation system 200 of FIG. 5 are given the same reference numerals. For example, the ablation system 200' includes substantially similar proximal portion 212 and middle portion 214 (not shown) features, functions and configurations of the ablation system 200. The ablation system 200' further includes a distal portion 216' having an expandable energy delivery member 250' including an electrode array 260 formed of a stretchable electrically conductive mesh, and a deflecting mechanism 270'. The deflecting mechanism 270' includes a pair of elongated polymeric flexures 224 coupled at respective transverse ends to the inflatable deflecting balloon 276, as shown in FIG. 10. As shown in FIG. 10, the deflecting mechanism or expandable-collapsible support structure 270' includes opposing first and second flexures 224 disposed within the tissue contacting member electrode array 260. The flexures 224 have a delivery configuration in which the flexures 224 are in a side-by-side configuration (FIG. 11A) aligned with the positioning member or inner elongate member 240. The flexures 224 have a deployed configuration in which a distal end of the first flexure 224 is positioned in the first corner portion of the tissue contacting member electrode array 260, and a distal end of the second flexure 224 is positioned in the second corner portion of the tissue contacting member electrode array 260. The first and second flexures 224 having arcuate outer surfaces 225 (FIG. 11B).

Additionally, a non-conductive elongated thread 229 may be operatively coupled to the respective distal ends of the flexures 224; the thread 229 further extends through the inner elongate member 240 (FIG. 10). The thread 229 is configured to assist with the disengagement of the deflecting mechanism 270', so that when the deflecting balloon 276 is deflated, the thread 229 is pulled (concurrently and/or subsequently to the deflation of the balloon) bringing the flexures 224 together.

FIGS. 11A-B illustrate the delivery configuration of the flexures 224 of the deflecting mechanism of the ablation system 200' of FIG. 10. The flexures 224 may be composed of any suitable biocompatible non-conductive material, such as PEEK or the like. The first and second flexures 224 each comprises one or more embedded conductors 226, each conductor 226 electrically connected to a respective portion of the tissue contacting member electrode array 260. The conductors 226 extend through a respective first and second flexure 224 and further extend through inner elongate member 240, which are operatively connected to an RF generator (not shown). The conductors 226 are electrically coupled to the electrode array 260 of the ablation system 200' for delivery of RF energy to the endometrial lining tissue. As better appreciated in the cross-sectional view of FIG. 11B, the conductors 226 are embedded in the flexures 224, and each flexures 224 include a respective arcuate (e.g., semi-circular) outer surface 225. In the side-by-side delivery configuration, the arcuate outer surfaces 225 of the first and second flexures 224 together define a cylindrical outer surface (FIG. 11B), and the distal ends of the first and second flexures 224 together define a tapered or rounded tip (FIG. 11A). At least one of the first and second flexures 224 comprises an embedded inflation lumen 223 fluidly coupled to an interior of the balloon 276. The inflation lumen 223 is coupled to a fluid and/or gas source for inflation of the balloon 276. As shown in FIGS. 11A-B, the deflated balloon 276 is disposed between the distal ends of the first and second flexures 224.

It should be appreciated that any of the above described embodiments may incorporate and/or use more than one deflecting mechanism 270 in combination with the electrode array 260. Further, it should be appreciated that any of the above described ablation systems may be used in combination with chemical ablation or any other suitable endometrial ablation system and methods.

Although particular embodiments have been shown and described herein, it will be understood that they are not intended to limit the disclosed inventions, and it will be apparent that various changes and modifications may be made (e.g., to the dimensions of various parts) without departing from the scope of the disclosed inventions, which are to be defined only by the claims and their equivalents. For instance, it will be appreciated that elements or components shown with any embodiment herein may be used on or in combination with other embodiments disclosed herein. The specification and drawings are, accordingly, to be regarded in an illustrative rather than restrictive sense.

What is claimed is:
1. An endometrial tissue treatment device, comprising:
an elongate positioning member; and
an energy applicator coupled to a distal end of the positioning member,
the energy applicator comprising a tissue contacting member and an expandable-collapsible support structure underlying the tissue contacting member,
the expandable-collapsible support structure comprising a substantially non-compliant elongate balloon disposed within a distal portion of the tissue contacting member that, when inflated within a uterus, has a lengthwise dimension oriented substantially transverse to the positioning member that spans a fundal wall of the uterus extending between a first corner portion of the tissue contacting member positioned in a first cornu of the uterus and a second corner portion of the tissue contacting member positioned in a second cornu of the uterus, such that the tissue contacting member is disposed between a distal facing surface of the inflated balloon and the fundal wall of the uterus, the inflated balloon having a widthwise dimension transverse to the lengthwise dimension, wherein the widthwise dimension of the inflated balloon is less than half the lengthwise dimension.

2. The endometrial tissue treatment device of claim 1, further comprising an elongate hollow delivery sheath having a distal portion configured for transcervical placement into the uterus, the delivery sheath having a lumen and an open distal end in communication with the delivery sheath lumen, wherein the respective positioning member and energy applicator are slidably disposed in the delivery sheath lumen so that the energy applicator slidably moves between a collapsed configuration in which the energy applicator is at least partially withdrawn through the open distal end of the delivery sheath and into the delivery sheath lumen, and an extended configuration in which the energy applicator is extended out the open distal end of the delivery sheath and at least partially self-expanded to conform to the uterus.

3. The endometrial tissue treatment device of claim 2, wherein the delivery sheath and positioning member are operatively coupled to an actuator that moves the positioning member relative to the delivery sheath to thereby move the energy applicator between the collapsed configuration and the extended configuration.

4. The endometrial tissue treatment device of claim 1, further comprising at least one inflation member having an inflation lumen fluidly coupled to an interior of the balloon, with a proximal end of the respective inflation member configured for fluidly coupling the respective inflation lumen with a source of inflation media.

5. The endometrial tissue treatment device of claim 1, further comprising an elongate tensioning member that is movable relative to the positioning member, the tensioning member having a distal end fixed to the balloon at an approximate lengthwise midpoint of the balloon.

6. The endometrial tissue treatment device of claim 5, wherein the distal end of the tensioning member comprises, or is otherwise connected to, a ring member that at least partially circumferentially surrounds the balloon at the approximate lengthwise midpoint of the balloon.

7. The endometrial tissue treatment device of claim 1, the support structure further comprising opposing first and second flexures disposed within the tissue contacting member, the flexures having a delivery configuration in which the flexures are in a side-by-side configuration aligned with the positioning member, and a deployed configuration in which a distal end of the first flexure is positioned in the first corner portion of the tissue contacting member, and a distal end of the second flexure is positioned in the second corner portion of the tissue contacting member, the first and second flexures having arcuate outer surfaces.

8. The endometrial tissue treatment device of claim 7, wherein in the side-by-side delivery configuration, the arcuate outer surfaces of the first and second flexures together define a cylindrical outer surface.

9. The endometrial tissue treatment device of claim 7, wherein in the side-by-side delivery configuration, the distal ends of the first and second flexures together define a tapered or rounded tip.

10. The endometrial tissue treatment device of claim 7, the first and second flexures each comprising one or more embedded conductors, each conductor electrically connected to a respective portion of the tissue contacting member.

11. The endometrial tissue treatment device of claim 7, wherein at least one of the first and second flexures comprises an embedded inflation lumen fluidly coupled to an interior of the balloon.

12. The endometrial tissue treatment device of claim 1, wherein the tissue contacting member is moisture permeable.

13. The endometrial tissue treatment device of claim 1, further comprising an actuator including a grip-style handle that is actuated by squeezing together a pair of pivotably connected grip members.

14. The endometrial tissue treatment device of claim 1, further comprising an aspiration lumen extending through the positioning member and having an open distal end located within the support structure.

* * * * *